United States Patent
Ligler et al.

(10) Patent No.: US 6,808,937 B2
(45) Date of Patent: Oct. 26, 2004

(54) DISPLACEMENT ASSAY ON A POROUS MEMBRANE

(75) Inventors: Frances S. Ligler, Potomac, MD (US); Anne W. Kusterbeck, Falls Church, VA (US); Sina Y. Rabbany, Great Neck, NY (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 385 days.

(21) Appl. No.: 09/907,888

(22) Filed: Jul. 13, 2001

(65) Prior Publication Data

US 2002/0028475 A1 Mar. 7, 2002

Related U.S. Application Data

(62) Division of application No. 08/583,912, filed on Jan. 11, 1996, now Pat. No. 6,750,031.

(51) Int. Cl.⁷ ............................................. G01N 33/543
(52) U.S. Cl. ................. 436/518; 435/287.6; 435/288.1; 435/288.5
(58) Field of Search ......................... 435/7.95, 4, 287.3, 435/287.6, 287.7, 287.9, 288.1, 288.2, 288.4, 288.5, 283.1, 288.7, 287.1, 7.92, 7.93, 7.94, 287.8, 287.2; 436/518, 524, 535, 538, 539, 540, 541, 66, 67, 174, 177, 178; 422/50, 55, 61, 68.1, 58, 69, 82.05, 99, 101, 102, 83

(56) References Cited

U.S. PATENT DOCUMENTS

| | | | | |
|---|---|---|---|---|
| 3,800,780 A | * | 4/1974 | Elliott | ........................ 128/2 F |
| 4,258,001 A | | 3/1981 | Pierce et al. | |
| 4,812,293 A | * | 3/1989 | McLaurin et al. | ............. 422/69 |
| 4,859,583 A | | 8/1989 | Heller | |
| 4,895,809 A | | 1/1990 | Schlabach et al. | |
| 4,916,056 A | | 4/1990 | Brown, III et al. | |
| 4,920,046 A | | 4/1990 | McFarland et al. | |
| 5,024,238 A | * | 6/1991 | Guirguis | ..................... 435/7.9 |
| 5,045,479 A | | 9/1991 | Newman et al. | |
| 5,183,740 A | | 2/1993 | Ligler et al. | |
| 5,206,177 A | | 4/1993 | DeLaCroix et al. | |
| 5,340,748 A | | 8/1994 | Baugher et al. | |
| 5,354,654 A | | 10/1994 | Ligler et al. | |
| 5,369,007 A | | 11/1994 | Kidwell | |
| 5,470,713 A | | 11/1995 | El Shami et al. | |
| 5,573,921 A | | 11/1996 | Behnke et al. | |
| 5,602,037 A | * | 2/1997 | Ostgaard et al. | .............. 436/69 |
| 6,016,712 A | * | 1/2000 | Warden et al. | ........... 73/864.21 |

OTHER PUBLICATIONS

"Kinetices of Antibody Binding at Solid– Liquid Interfaces in Flow", Wemhoff et al., J. Immunol. Methods, 156 (1992) 223–230.
Ramp Urine hcG Assay brochure (1986), RMP002 30M 0186.
GRAnite Diagnostics Inc., "Description of the E–Z Screen Test System" Brochure, Oct. 7, 1985.
"Enzyme", Analytical Chemistry, vol. 56, No. 8, Jul 1984, 920A–922, 924A, 926A, 928A, 930–931A.
" Mutilayer Film Elements for Clinical Analysis: General Concepts", Curme et al., Clin. Chem., 24/8, 1335–1341.
"Multilayer Flourescent Immunoassay Technique", Greener et al., Clin. Chem., 34, (1989) 1865–1869.

* cited by examiner

Primary Examiner—Christopher L. Chin
Assistant Examiner—Ann Y. Lam
(74) Attorney, Agent, or Firm—John J. Karasek; Joseph T. Grunkemeyer

(57) ABSTRACT

Displacement assays, under non-equilibrium conditions, are performed by flowing a liquid sample through a membrane having binding elements with binding sites saturated with a labelled form of the analyte. Analyte in the sample displaces, under non-equilibrium conditions, the labelled form of the analyte from the membrane. The displaced labelled form of the analyte may then be detected.

2 Claims, 6 Drawing Sheets

DISPLACEMENT ASSAY ON A POROUS MEMBRANE

This is a of divisional application Ser. No. 08/583,912, filed Jan. 11, 1996 now U.S. Pat. No. 6,750,031, the entirety of which is herein incorporated by reference.

BACKGROUND OF THE INVENTION

1. Field of the Invention

The present invention relates generally to assays and more specifically to displacement-type assays.

2. Description of the Background Art

U.S. Pat. No. 5,183,740, incorporated in its entirety herein for all purposes, describes a flow immunoassay system and method for performing displacement immunoassays. In a displacement assay, unlike a competitive assay, the antibody is exposed to labelled analyte prior to exposure to analyte. The analyte is in contact with the antibody and labelled, bound analyte an insufficient amount of time to establish equilibrium.

Because no time needs to be dedicated to establishing equilibrium, displacement assays are faster than competitive assays. A displacement assay, however, generally provides a smaller signal than a competitive assay. In a displacement assay, the available binding sites of the antibody are saturated or nearly saturated with labelled analyte before the unlabelled analyte is added. Since equilibrium (with labelled analyte and unlabelled analyte continually binding, releasing and competing with each other for rebinding to the available binding sites on the antibody in a steady state) has not been achieved, most of the labelled analyte in a displacement assay remains bound to the antibody and unable to provide a signal.

The relatively small signal provided by the displacement assay places an additional value on assuring the consistency of assay conditions. The bead-containing columns described in U.S. Pat. No. 5,183,740 for displacement assays must be carefully stored, prepared, and loaded to assure chemical and physical consistency (i.e., porosity, avoidance of channeling) from test to test. The need for this careful preparation and testing increases the labor, skill, and costs needed to perform accurate displacement assays. Additionally, the problems associated with the use of bead-containing columns limit the lower detection limit for displacement assays.

In studies performed at US Drug Testing, Inc. (Rancho Cucamonga, Calif.), better results for a displacement assay were achieved using tall, thin columns of beads coated with an antibody and labelled antigen than with short, wide columns. Furthermore, the efficiency with which the labelled antigen dissociated from antibody in the presence of unlabelled antigen was greater when flow rates were reduced and the antigen had more time to interact with the immobilized complex (Wemhoff et al. *J. Immunol. Methods,* 223–230, 1992). Both of these sets of experiments suggested that immobilization of the antibody and labelled antigen on a porous membrane would not provide a suitable matrix for the displacement assay since this geometry would not allow sufficient time, under flow conditions, for the antigen to interact efficiently with the complex to displace detectable amounts of the labelled antigen.

U.S. Pat. No. 5,369,007, to David A. Kidwell discloses a displacement assay in which samples pass through a membrane having an antibody immobilized thereon. The binding sites of the immobilized antibody are bound to an enzymatically labelled analyte. Analyte from the sample displaces the labelled analyte, causing the labelled analyte and the remainder of the sample to pass into a superabsorbent layer. The superabsorbent layer contains a substrate for the enzymatic label and any needed indicator. The Kidwell patent, however, teaches the need for a flow rate of about 0.02 ml/min and interaction times of about 1 to 5 min to assure a detectable interaction between the analyte and the antibody. In many situations, even faster results are desirable. Additionally, the Kidwell microassay card is not reusable.

SUMMARY OF THE INVENTION

Accordingly, it is an object of this invention to perform bioassays capable of detecting minute quantities of an analyte in under one minute.

It is another object of the present invention to quickly perform bioassays in a format that allows reuse of the matrix that selectively binds the analyte.

These and additional objects of the invention are accomplished by quickly flowing a sample past a non-absorbent membrane having a binding element covalently bound thereto to form attachment sites for the analyte. The available attachment sites are essentially saturated with a labelled form of the analyte. Nonspecific binding sites are blocked to prevent nonspecific binding. Additionally, the sample flows past the membrane at a rate greater than that needed to achieve equilibrium between the dissociation of labelled analyte from the binding sites and the attachment of analyte (labelled or unlabelled) thereto. The processed sample is then analyzed for the presence of any labelled antigen that the unlabelled analyte has displaced from its binding site. This analysis can be qualitative or quantitative.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements, wherein.

DESCRIPTION OF THE PREFERRED EMBODIMENTS

Figure 1:
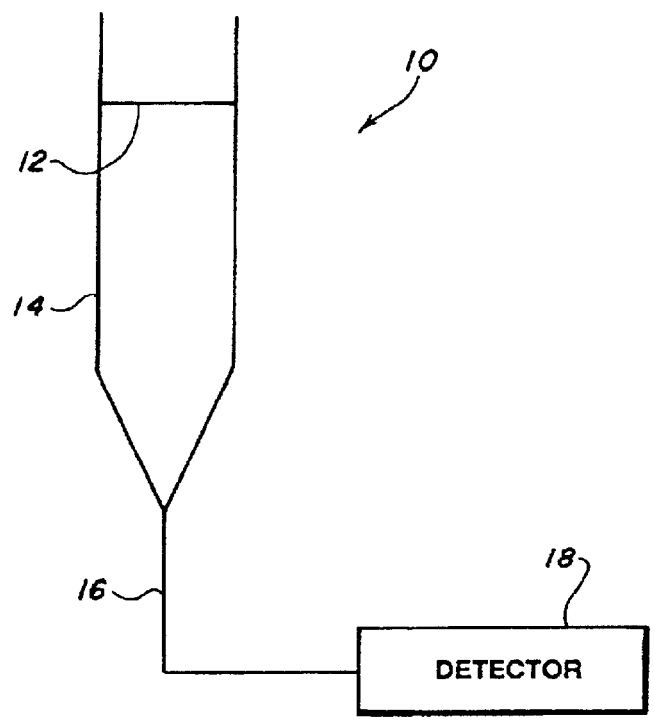
FIG. 1 schematically illustrates a device according to the present invention.

Membranes useful in the present invention are typically non-absorbent (with respect to aqueous materials) materials. The non-absorbent membrane assists in providing a fast flow-through rate. Additionally, the use of a non-absorbent membrane allows the membrane, once used, to be readily rinsed of sample and reused. If displacement has occurred, reloading with labelled analyte is an option.

Typically, membranes useful in the present invention have thicknesses, exposed surface areas, and porosities that allow detection of the analyte with an interaction time of about 0.1 sec to about 30 seconds, and typically about 1 sec to about 15 seconds, between a sample suspected of containing of the analyte and the membrane having a labelled analyte of the analyte thereon. Generally, the pore sizes in the membrane are about 0.2–1.0 microns, and are typically about 0.45 microns. Of course, other pore sizes may be used to achieve the desired interaction time. Likewise, the thickness and surface area of the membrane can be adjusted to provide the desired interaction time.

Any non-absorbent membrane, of appropriate pore size and density of sites for immobilizing binding elements for the analyte, may be used. For example, the membrane may be a polyamide (e.g., Nylon™ membranes such as Immunodyne ABC™ (a Nylon™ 6,6 membrane made by Pall Biosupport, Port Washington, N.Y.)) or a polyvinylidine fluoride, such as Immobilon™ or Durapore™ membranes made by Millipore, Bedford, Mass. Other suitable membranes include, but are not limited to, cellulose, nitrocellulose, silica fiber, aluminum oxide, and polyvinyl chloride.

Binding elements may be immobilized on the selected membrane in any manner that assures the availability on the immobilized binding element of at least one binding site for selectively binding the labelled analyte and target analyte in an aqueous medium. Several methods for attaching binding elements to the membranes are well-known and therefore will not be specifically described herein. The binding element may be immobilized either throughout the thickness of the membrane, or on only one or both surfaces thereof.

The binding element may be any substance that can be immobilized on the membrane and that specifically binds the target analyte and its labelled analog. Binding elements include, but are not limited to, lectins, antibodies, antibiotics, and binding proteins other than antibodies and antibiotics.

Once the binding elements have been immobilized on the membrane, their available binding sites for selectively binding with the analyte will usually be essentially saturated with a labelled analog of the analyte (denoted herein as a "labelled analyte"). Saturation of the available binding sites with the labelled analyte enhances sensitivity by assuring that the maximum number of analyte molecules will displace labelled analytes, rather than binding directly to unoccupied binding sites.

The membrane may be oriented in any manner with respect to sample flow that allows the sample to flow past the complex of binding element and labelled analyte on the membrane over the desired interaction time. For example, the sample may flow through and essentially normal to the plane of the membrane. Alternatively, the membrane may be configured as a dipstick and the sample allowed to flow laterally through the membrane, for example by capillary action. In another alternative, the membrane support may be a hollow fiber configured so the sample flows along the hollow center before passing through the membrane. In any embodiment of the present invention, the flow of the sample through the membrane may be passive (i.e., gravitational or capillary flow) or active (flow resulting entirely or partly from the action of a flow pump, manual pressure, or vacuum).

Any label useful in assays for the analyte may be used to label the analyte. Fluorophores are particularly useful labels. Suitable fluorophores include, but are not limited to Fluorescein, Cadaverine, Texas Red™ (Molecular Probes, Eugene, Oreg.) and Cyanine 5™ (BDS, Pennsylvania). If used, the fluorophore label is typically one that is detectable in the visible to near infrared range.

Once the sample has completed its interaction with the membrane having the immobilized binding element-labelled analyte thereon, the processed sample (e.g., the effluent from a sample column or the portion of the sample that has passed through and beyond the labelled portion of a test strip) is then analyzed to determine the concentration of displaced labelled analyte. The detection means for this analysis includes a readout for informing the user that a threshold amount of the label has been detected in the sample. When the label is fluorescent, the detection means also includes a light source for exciting the fluorophore-labelled analytes. The detection system can use various methods of optical measurement, including but not limited to a spectrophotometer, infrared spectrometer, fluorimeter, optical biosensor, or the eye.

The present invention is useful in the detection, in aqueous media, of any analyte that specifically binds to the binding element. The invention may be used, for example, to detect the presence of analytes in body fluids (blood, semen, saliva, urine, etc.), water, pharmaceutical preparations, environmental samples, aerosols, foods, and beverages. If the sample suspected of containing the analyte is originally in a viscous liquid, solid, gaseous state, the sample is preferably further dissolved in water before being exposed to the membrane.

Multiple binding elements for multiple analytes can be immobilized on a single membrane. Membranes containing the same or a different binding element can be arranged in stacks. Where multiple binding elements for multiple analytes are used, different labels on the labelled analytes can be used to distinguish which analyte is present.

FIG. 1 schematically shows a device 10 according to the present invention where the membrane is normal to sample flow. Membrane 12, with binding elements covalently bound or otherwise immobilized thereto and available binding sites saturated with a labelled analyte of the analyte, is positioned across column 14. An aqueous sample entering the top of column 14 flows through membrane 12. Analyte in the sample interacts with membrane 12 and displaces the labelled analyte from membrane 12. The labelled analyte, if it does not displace another labelled analyte or unlabelled analyte from the membrane, joins the effluent from column 14. The aqueous sample effluent from column 14 then enters line 16, which carries the effluent to detector 18 for detecting the presence of the labelled analyte in the effluent from column 14.

Figure 2:
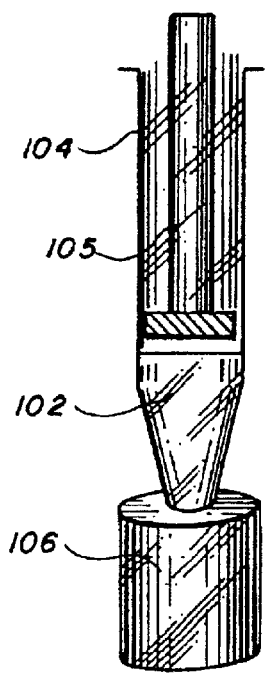
FIG. 2 schematically illustrates an alternative embodiment of a device according to the present invention.

FIG. 2 shows an alternative embodiment of the present invention, where the membrane is also normal to sample flow. Porous membrane 102, with binding elements covalently bound or otherwise immobilized thereto and available binding sites saturated with a labelled analyte of the analyte, is positioned across column 104 having an open tip. To prevent the flow of sample between the outer edge of membrane 102 and the inner wall of column 104, the membrane typically extends fully across the width of column 104. The open tip of column 104 is inserted into the top of container 106 (typically through a septum (not shown)), which holds a sample suspected of containing the analyte. Suction means 105 can apply a vacuum to pull sample from container 106 through membrane 102 into column 104. Any label in the column may be detected by a detection means external to the column. To facilitate this external detection, column 104 is preferably transparent to, or includes a suitably placed window transparent to, the energy used for detection.

Figure 3:
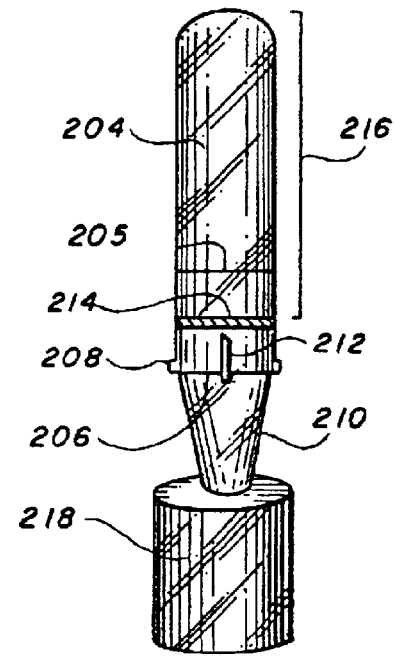
FIG. 3 schematically illustrates another alternative embodiment of a device according to the present invention.

Although FIG. 2 shows the suction means as a plunger and column 104 as the syringe housing the plunger, other vacuum arrangements are possible. For example, FIG. 3 shows a design similar to that used by Vacuutainers™.

Evacuated tube 204 has porous membrane 205, with binding elements covalently bound or otherwise immobilized thereto and available binding sites saturated with a labelled analogue of the analyte, thereacross. To prevent the flow of sample between the outer edge of porous membrane 205 and the inner wall of evacuated tube 204, the membrane typically extends fully across the width of evacuated tube 204. The open end of evacuated tube 204 is sealed by cap 206 having flange 208 extending about the rim of open end of tube 204. Tip 210 extends from cap 206 opposite to hollow needle 212, which also extends from cap 206. Needle 212 extends to near septum 214 when tube 204 is placed, with only slight pressure, within flange 208 in a first position. Septum 214 maintains the vacuum in the portion 216 of tube 214. Although septum 214 is essentially impermeable to gas or liquid, it is punctured by needle 212 once tube 204 is fully inserted into flange 208 in a second position. Upon the puncture of septum 214, the vacuum within portion 216 draws liquid from sample container 218 through tip 210, into hollow needle 212, through membrane 205 and into the part of portion 216 between the membrane 205 and the closed end. Any label within the part of portion 216 between the membrane 205 and the closed end can be detected as with other embodiments of the invention. To assure that needle 212 does not puncture membrane 205, the distance between the bottom of septum 214 and the bottom of membrane 205 should be greater then the height of needle 212. This embodiment of the invention assures that the flow across membrane 205 is consistent from sample to sample.

Having described the invention, the following examples are given to illustrate specific applications of the invention including the best mode now known to perform the invention. These specific examples are not intended to limit the scope of the invention described in this application.

EXAMPLES

Example 1

TNT Detection

To prepare the membranes, the monoclonal 11B3 antibody (mouse lgG$_1$) with specificity for TNT (trinitrotoluene) was immobilized onto the Immunodyne® ABC membrane with a pore size of 0.45 $\mu$m. The 11B3 antibody, 100 $\mu$l of a 2 nmol/ml solution in phosphate buffered saline (PBS), was attached to the membrane by either placing the solution in a test tube, with subsequent addition of the membrane, or pipetting the antibody into a column that already contained the membrane. Whether in a column or a test tube, membranes were incubated with the antibody for four hours at room temperature. Following incubation, the antibody solution was removed. Membranes exposed to antibody in a test tube were placed in a column. Any unreacted binding sites on the membrane were blocked with the addition of 100 $\mu$l of 1M Tris for approximately 30 minutes. To reduce nonspecific binding, the membranes were drained and washed three times with PBS containing 0.01% Triton X-100® detergent.

The labelled analyte was prepared by attaching the fluorophore CY5® (BDS, Pennsylvania) to trinitrobenzyl cadaverine (CY5-TNB). To saturate the antibody binding site with the labelled antigen, a solution of the CY5-TNB (4 nmoles in 50 $\mu$l PBS) was added to each column, and the columns were placed on a rocking bed overnight. The columns were connected to the fluorimeter and, washed briefly. Samples were introduced at a flow rate of 1 mL/min. Analyte injections were made in triplicate with concentrations ranging between 18.75 ng/mL and 1200 ng/mL. FIG. 2 illustrates data obtained for a membrane assay prepared with the test tube incubation method. A fluorescence signal peak was obtained at all analyte concentrations which was proportional to the amount of analyte added to the column.

FIG. 3 represents data from a membrane assay prepared by saturating the immobilized antibody with labelled analyte in the column as opposed to in a test tube. Again, an increase in signal intensity with increasing analyte concentration was observed. However, a plateau was seen between an analyte concentration of 700 ng/mL and 1200 ng/mL where a negligible increase in signal intensity was observed despite a two-fold increase in analyte concentration suggesting that there is less labelled analyte on the membrane available for displacement, compared to the membrane prepared in the test tube.

Figure 4:
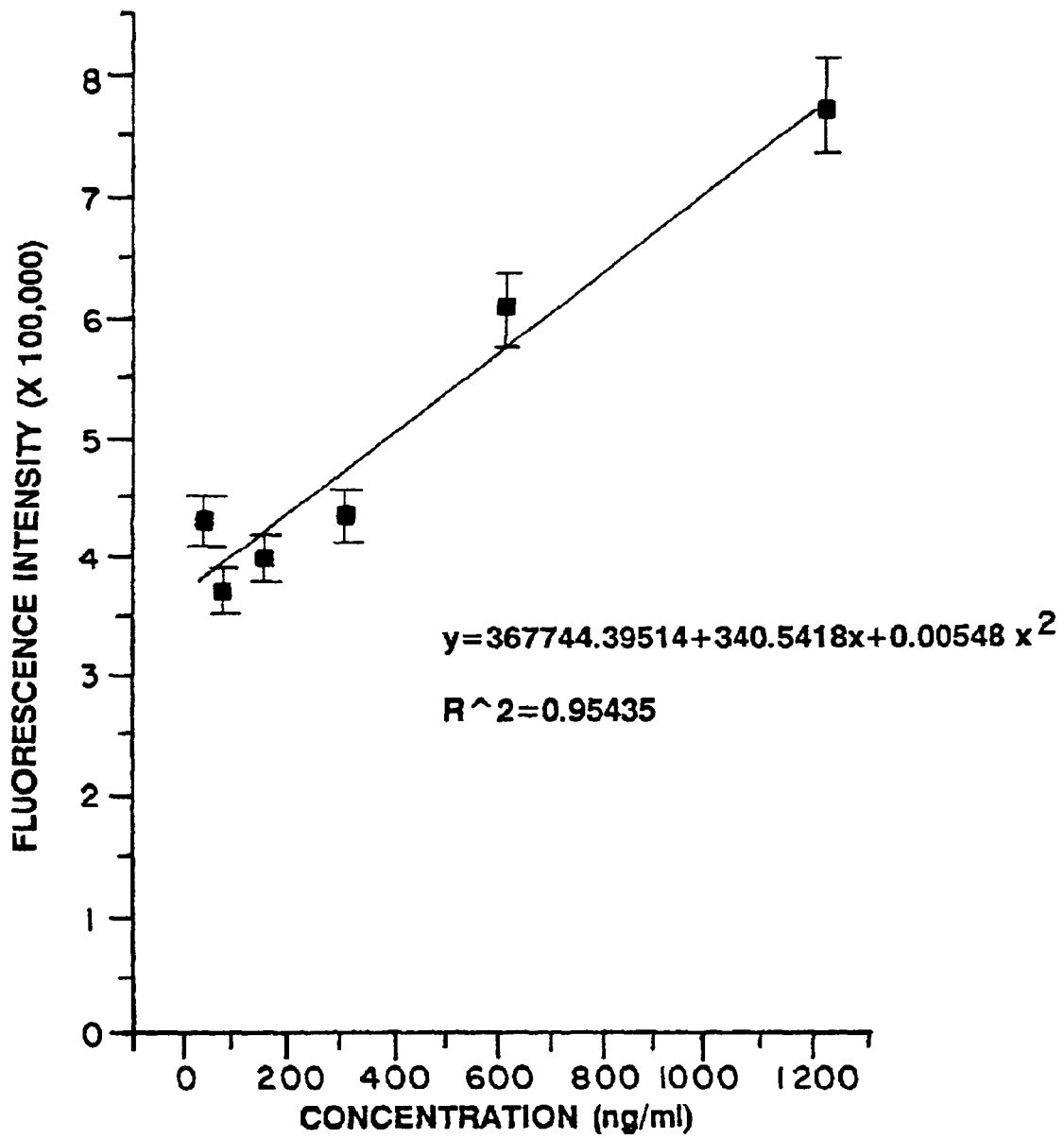
FIG. 4 is a graph of data from a membrane assay, in accordance with the present invention, in which the membrane was prepared by the test tube incubation method.

Both FIGS. 3 and 4 demonstrate reproducible results, with minimal standard error as indicated by the error bars. Assay times were fast with the exact time being simply a function of the flow rate (1 mL/min in this case) and the length of tubing between the analyte introduction site and the fluorimeter flow cell. For these experiments, signals were generated less than 1 minute from the time of sample introduction.

Example 2

Detection of RDX

Similar experiments were conducted whereby a monoclonal antibody with specificity for the explosive, cyclonite (RDX), was immobilized onto the membrane. The procedure for immobilization was identical to the one used for the anti-TNT antibody. However, 100 $\mu$l of 0.5% casein was used instead of Tris in order to block the remaining binding sites on the membrane. FIG. 4 represents data from a single membrane assay prepared by saturating the antibody directly in the column. A linear relationship between signal intensity and analyte concentration is observed. The lower limit of detection for this assay is at 5 ng/ml which corresponds to part per billion (ppb) levels.

II. Displacement Dipstick Studies

The main objective of these experiments was to design a qualitative membrane-based immunoassay for the detection of a target analyte in solution. The tests rely the displacement immunoassay to work on the Immunodyne membranes with the fluid flowing through them membranes laterally as opposed to perpendicular to the membrane as described above. Transported by capillary action, the fluid conducts the analyte in the sample to the immobilized antibody-labelled analyte complex and transports the displaced labelled analyte further along the membrane strip. The dipstick displacement assay is not only dependent upon the ability of the target analyte to displace the labelled analyte from the immobilized antibody but also on several other factors such as the rate of the capillary action of the mobile phase and the rates of transport of analyte and labelled analyte through the membrane.

Figure 5:
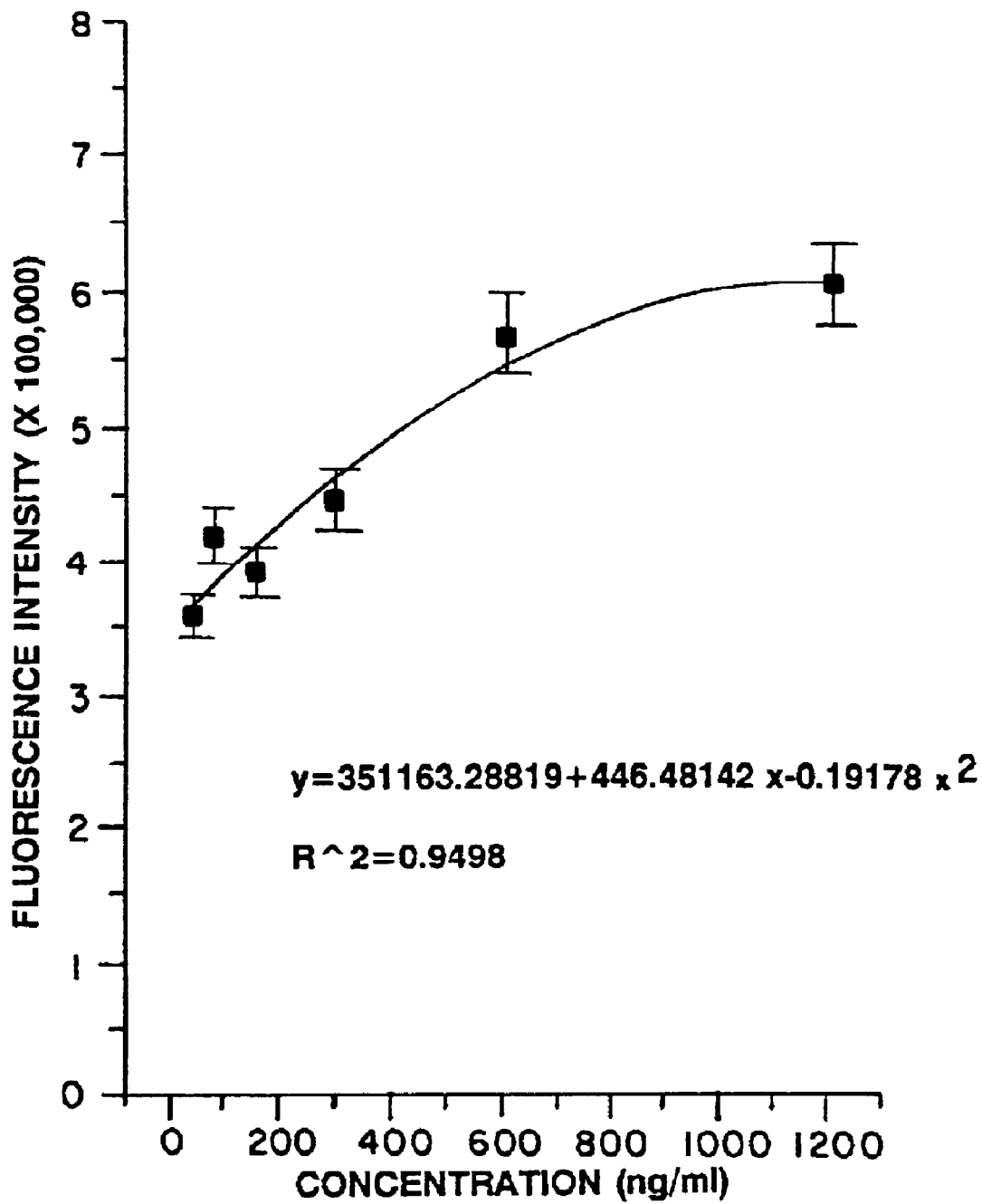
FIG. 5 is a graph of data from a membrane assay, in accordance with the present invention, in which the membrane was prepared by saturating the immobilized antibody with labelled analyte in the column as opposed to in a test tube.

FIG. 5 provides a schematic of the experimental protocol.

First, in step (a), strips 100 were cut from an ABC Immunodyne® membrane 110 that were either 30×5 mm or 50×10 mm. A monoclonal antibody specific for TNT (11B3) in concentrations ranging from 2 to 10 nmol/ml was placed in 5 $\mu$L droplets onto the membrane strips and allowed to immobilize for thirty minutes. In step (b), strips 100 were then soaked, using test tube 112, in a Tris solution for about an hour to block any other covalent binding sites. A washing of membrane strips 100 followed that consisted of three consecutive exposures to PBS containing 0.01% Triton X-100 to wash away any excess TNT antibody (step (c)). After a final wash with PBS, CY5-TNB labelled analyte, in excess of five-to-thirty times the molar amount of antibody, was applied in 6.5 $\mu$L droplets onto the antibody and incubated overnight (step (d)). In step (e), strips 100 were then washed in PBS containing 2.5% ethanol, and 1% Tween 20™ for ten minutes in order to remove nonspecifically bound labelled analyte. In step (f), before drying, strips 100 were put into a solution of 100 mM trehalose dihydrate in phosphate buffer for ten minutes. Finally, in step (g) the strips were dried at room temperature. The displacement assay (step (h)) was conducted by dipping the end of membrane strip 100 in TNT solution 114, 116, 118, or 120 (of the concentration specified in FIG. 5, step (h)), and allowing capillary action to bring the target analyte up to the antibody/labelled analyte complex for displacement. A 650 nm laser (not shown) connected to a fluorescence detector was used to look for any displaced labelled analyte (Cy5-TNB) on membrane strip 100.

Figure 6:
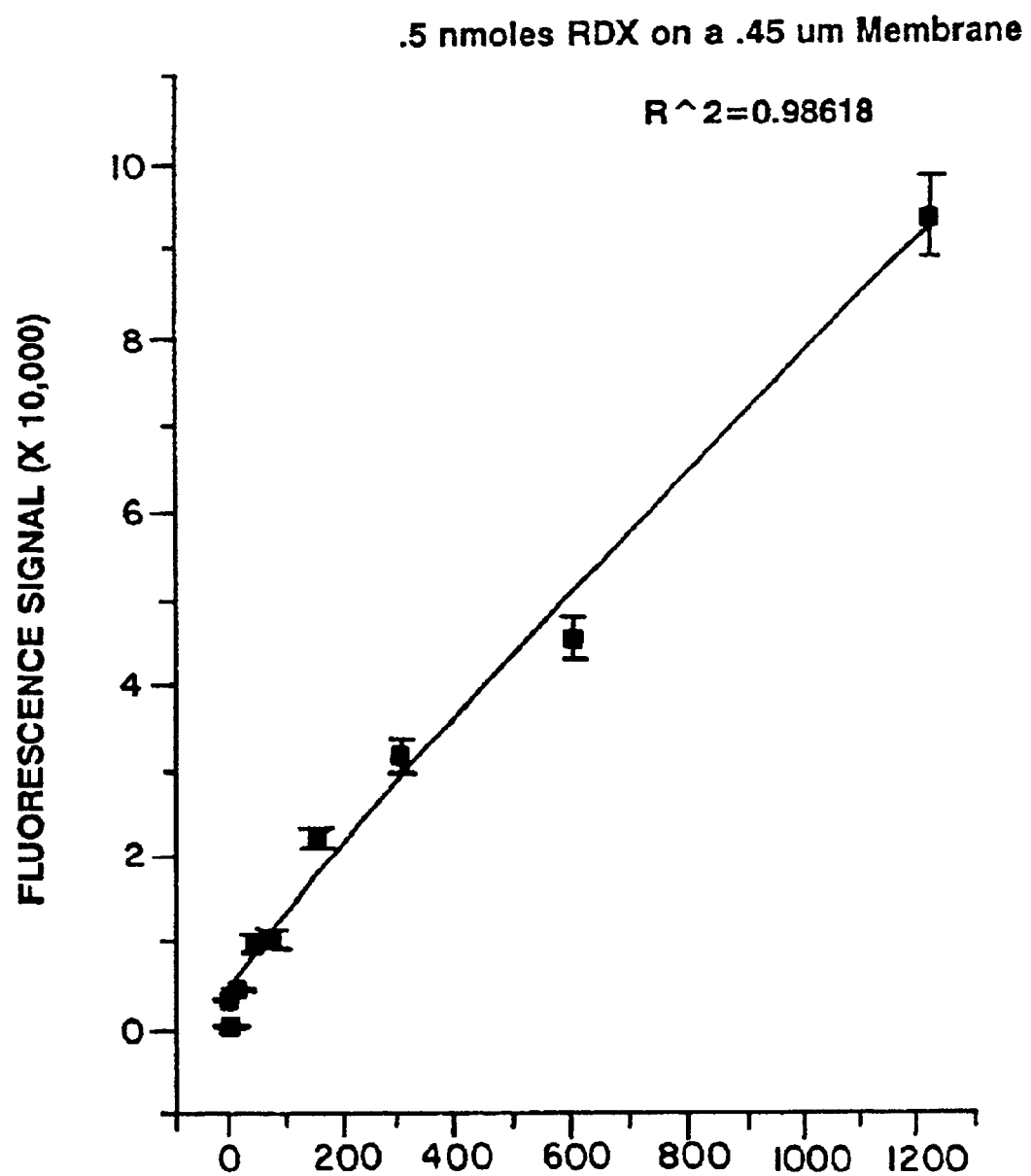
FIG. 6 is a graph of data from a single membrane assay, according to the present invention, prepared by saturating the antibody directly in the column.
Figure 7:
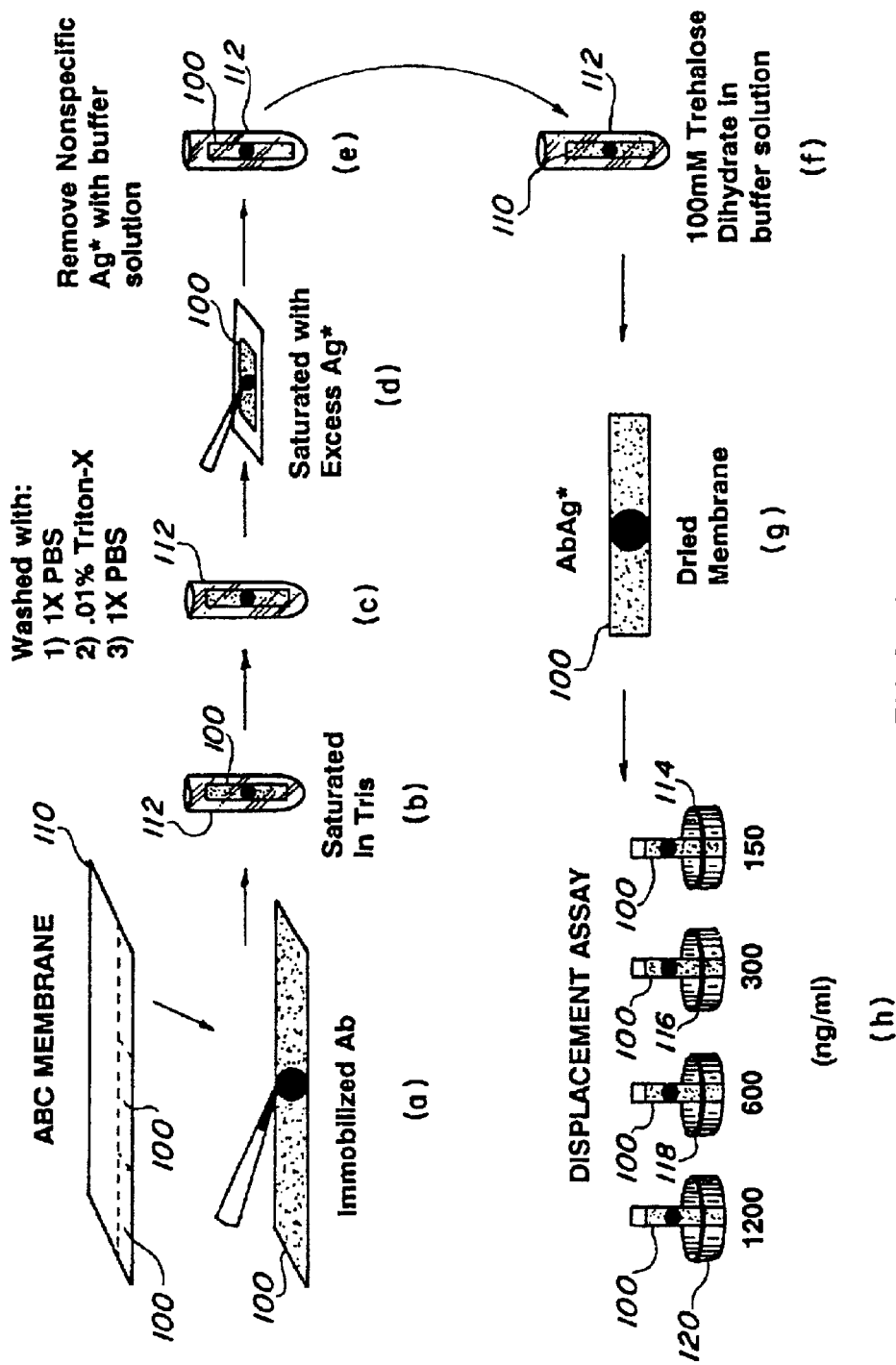
FIG. 7 is a flowchart schematically illustrating an embodiment of an assay according to the method of the present invention.
Figure 8A:
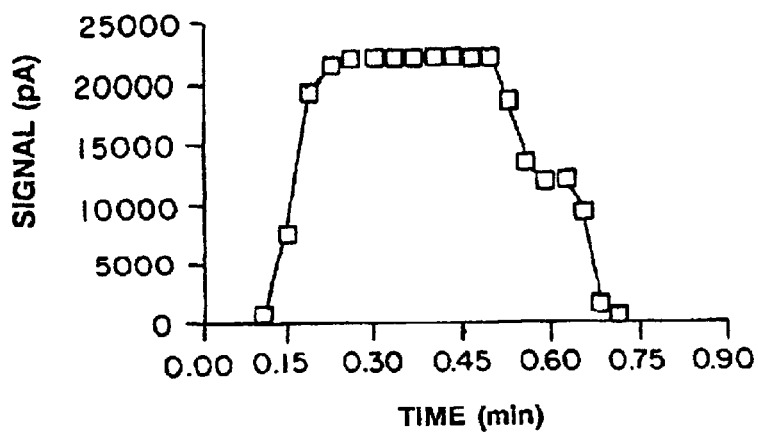
FIGS. 8a, 8b, and 8c show the results obtained from assay performed in accordance with the method flowcharted in FIG. 7.
Figure 8B:
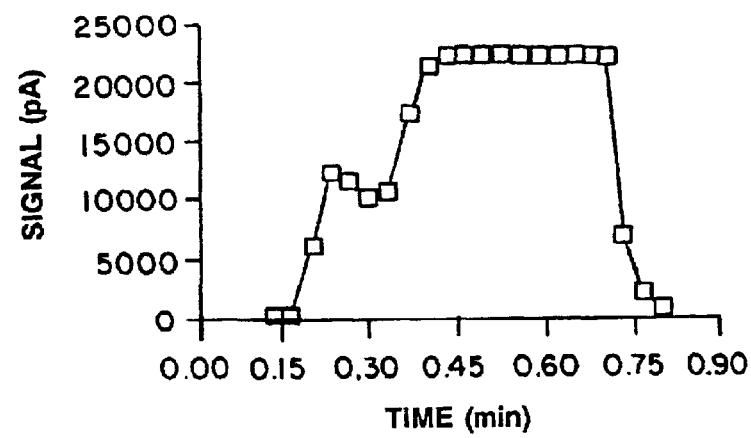
Figure 8C:
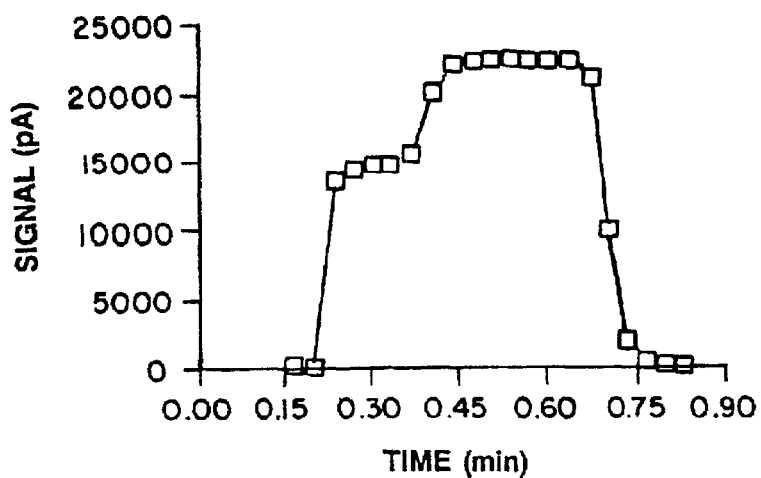

In the first experiment, TNT antibody at a concentration of 2 nmol/ml was placed at the center of a 3×0.5 cm, rectangular membrane strip and was saturated by five times excess CY5-TNB. The strip was then dipped into a sample solution containing 300 ng/ml TNT. FIG. 6*a* represents this strip when the dipped end is held under the laser first (left side). The higher plateau indicates the fluorescence from the CY5-TNB bound to the immobilized antibody. A shoulder is evident to the right of the higher plateau, indicating displacement of the labelled analyte from the antibody. FIG. 6*b* shows this same strip optically interrogated in the reverse direction where the dipped end is on the right. Another membrane strip, also having 2 nmol/ml of immobilized anti-TNT antibody was treated identically and exposed to the same 300 ng/ml TNT solution. After placing it under the laser with the dipped end on the right, the data shown in FIG. 6*c* was obtained. These experiments were conducted by manually moving the membrane strip along the laser path. "Time" on the x-axis refers to scanning time and has no relation to assay time.

Obviously, many modifications and variations of the present invention are possible in light of the above teachings. It is therefore to be understood that, within the scope of the appended claims, the invention may be practiced otherwise than as specifically described.

What is claimed is:

1. A device for the immunoassay of an aqueous sample suspected of containing a target analyte, comprising:

a container, said container including an open end and a closed end;

a cap within which said open end of said container may be fitted in a first position in which the closed end of said container is a first distance from said cap and in a second position in which the closed end of said container is a second distance from said cap, said second distance being less than said first distance;

a tip for receiving said aqueous sample extending outwardly from said cap;

a hollow needle extending from said cap in a direction opposite to said tip;

a septum extending across the width of said container, said septum being positioned between said closed end of said container and an end of said needle distal to said cap when said container is seated in said first position, said septum being essentially impermeable to fluid;

a porous membrane positioned between said septum and said closed end of said container, said membrane extending across the width of said container, and an evacuated reservoir between said membrane and said closed end, said membrane having binding elements immobilized thereon, each of said binding elements having at least one binding site capable of specifically binding to said target analyte, essentially all of said binding sites on said binding elements being either occupied by a labelled analog of the target analyte to form complexes of membrane-immobilized binding elements and labelled analogs; and a detector for detecting the presence of said labelled analog in said reservoir;

said hollow needle being positioned so as to puncture said septum, but not said membrane, when said container is in said second position.

2. The device of claim 1, further comprising a sample holder for holding a liquid sample therein, wherein said puncture of said septum causes liquid sample from sample holder to flow through said open end, through said membrane, and into said reservoir.

* * * * *